(12) United States Patent
Lowe et al.

(10) Patent No.: US 9,827,082 B2
(45) Date of Patent: Nov. 28, 2017

(54) FLUORIDE RELEASING BITE PLATE

(71) Applicant: ORTHOACCEL TECHNOLOGIES INC., Bellaire, TX (US)

(72) Inventors: Michael K. Lowe, Bellaire, TX (US); Dwight Schnaitter, Bellaire, TX (US)

(73) Assignee: OrthoAccel Technologies, Inc., Bellaire, TX (US)

( * ) Notice: Subject to any disclaimer, the term of this patent is extended or adjusted under 35 U.S.C. 154(b) by 34 days.

(21) Appl. No.: 14/182,988

(22) Filed: Feb. 18, 2014

(65) Prior Publication Data
US 2014/0242535 A1  Aug. 28, 2014

Related U.S. Application Data (60) Provisional application No. 61/769,507, filed on Feb. 26, 2013, provisional application No. 61/832,358, filed on Jun. 7, 2013.

(51) Int. Cl.
| A61C 3/00 | (2006.01) |
| A61C 19/06 | (2006.01) |
| A61C 7/00 | (2006.01) |

(52) U.S. Cl.
CPC ............ *A61C 19/063* (2013.01); *A61C 7/008* (2013.01); *A61C 19/066* (2013.01)

(58) Field of Classification Search
CPC ........... A61C 7/08; A61C 7/36; A61C 19/063; A61C 17/20
USPC ................ 433/18, 24, 80, 86, 215, 216, 229
See application file for complete search history.

(56) References Cited

U.S. PATENT DOCUMENTS

| 4,044,762 | A | | 8/1977 | Jacobs |
| 4,127,125 | A | * | 11/1978 | Takemoto et al. ............... 604/22 |
| 4,162,576 | A | * | 7/1979 | Takemoto et al. ............... 433/89 |
| 5,037,294 | A | * | 8/1991 | Bergersen ................ A61C 7/08 264/16 |
| 5,198,220 | A | | 3/1993 | Damani |
| 5,718,924 | A | * | 2/1998 | Braden et al. ................. 424/673 |
| 6,009,589 | A | | 1/2000 | Driessen et al. |
| 7,458,810 | B2 | * | 12/2008 | Bergersen ................ A61C 7/08 433/6 |
| 7,850,453 | B2 | * | 12/2010 | Jodaikin ............... A61C 19/063 433/215 |
| 8,287,277 | B2 | * | 10/2012 | Jodaikin ............... A61C 19/063 433/80 |
| 2002/0081556 | A1 | * | 6/2002 | Tseng et al. ................... 433/229 |
| 2005/0003319 | A1 | * | 1/2005 | Kuo ................................... 433/6 |
| 2008/0227046 | A1 | | 9/2008 | Lowe et al. |

(Continued)

OTHER PUBLICATIONS

Arbabzadeh-Zavareh, F., Recharge pattern of contemporary glass ionomer restoratives, Dent Res J (Isfahan). Mar. 2012; 9(2):139-45.

(Continued)

*Primary Examiner* — Eduardo C Robert
*Assistant Examiner* — Matthew Saunders
(74) *Attorney, Agent, or Firm* — Boulware & Valoir (57) ABSTRACT

The present disclosure relates to bite plates for use with various orthodontic remodeling devices. A bite plate that releases fluoride during use, thus encouraging remineralization on enamel is described. Additionally, bite plates with a colorant or color-changing matrix that serve as indicators for fluoride concentration are also described.

10 Claims, 10 Drawing Sheets

(56) References Cited

U.S. PATENT DOCUMENTS

| | | | |
|---|---|---|---|
| 2009/0042161 A1* | 2/2009 | Jodaikin | A61C 19/063 433/80 |
| 2009/0068123 A1* | 3/2009 | Takei et al. | 424/52 |
| 2010/0055634 A1* | 3/2010 | Spaulding et al. | 433/5 |
| 2011/0104635 A1* | 5/2011 | Jodaikin | A61C 19/063 433/80 |
| 2012/0171637 A1* | 7/2012 | Wu | 433/141 |
| 2012/0285574 A1 | 11/2012 | Mason | |
| 2012/0322018 A1 | 12/2012 | Lowe et al. | |
| 2013/0108982 A1* | 5/2013 | Jodaikin | A61C 19/063 433/80 |
| 2014/0026811 A1* | 1/2014 | Patel | A46B 11/001 118/268 |

OTHER PUBLICATIONS

Austina, R.S., et al., The effect of increasing sodium fluoride concentrations on erosion and attrition of enamel and dentine in vitro, J Dent. Oct. 2010; 38(10):782-7.

Beltran-Aguilar, E.D., et al., Prevalence and Severity of Dental Fluorosis in the United States, 1999-2004, NCHS Data Brief No. 53, Nov. 2010., available online at cdc.gov/nchs/data/databriefs/db53.htm.

De Francisco, L.M., et al., Development and characterization of gelatin and ethylcellulose microparticles designed as platforms to delivery fluoride, Drug Dev Ind Pharm. 2012.

Lin D.M., A polymeric device for delivery of anti-microbial and anti-fungal drugs in the oral environment: effect of temperature and medium on the rate of drug release, Dent Mater. Nov. 2003; 19(7):589-96.

Lynch, E., et al., Multi-component bioactive glasses of varying fluoride content for treating dentin hypersensitivity, Dent Mater. Feb. 2012; 28(2):168-78.

Rosenblatt, A., et al., Silver Diamine Fluoride: A Caries "silver-fluoride bullet", J Dent Res. Feb. 2009; 88(2):116-25.

Wu, N., et al., Effect to demineralization and remineralization of enamel surface by fluorine, Oct. 2012; 30(5):493-7.

Baturina, O., Development of a sustained fluoride delivery system, Angle Orthod. Nov. 2010; 80(6):1129-35.

* cited by examiner

FLUORIDE RELEASING BITE PLATE

PRIOR RELATED APPLICATIONS

This application claims priority to 61/769,507, filed Feb. 26, 2013, and 61/832,358, filed Jun. 7, 2013, both incorporated by reference in their entireties for all purposes herein.

FEDERALLY SPONSORED RESEARCH STATEMENT

Not applicable.

REFERENCE TO MICROFICHE APPENDIX

Not applicable.

FIELD OF THE DISCLOSURE

The invention relates to biteplates for use with various orthodontic remodeling devices, wherein the bite plate releases fluoride during use, thus encouraging remineralization on enamel.

BACKGROUND OF THE DISCLOSURE

Figure 1:
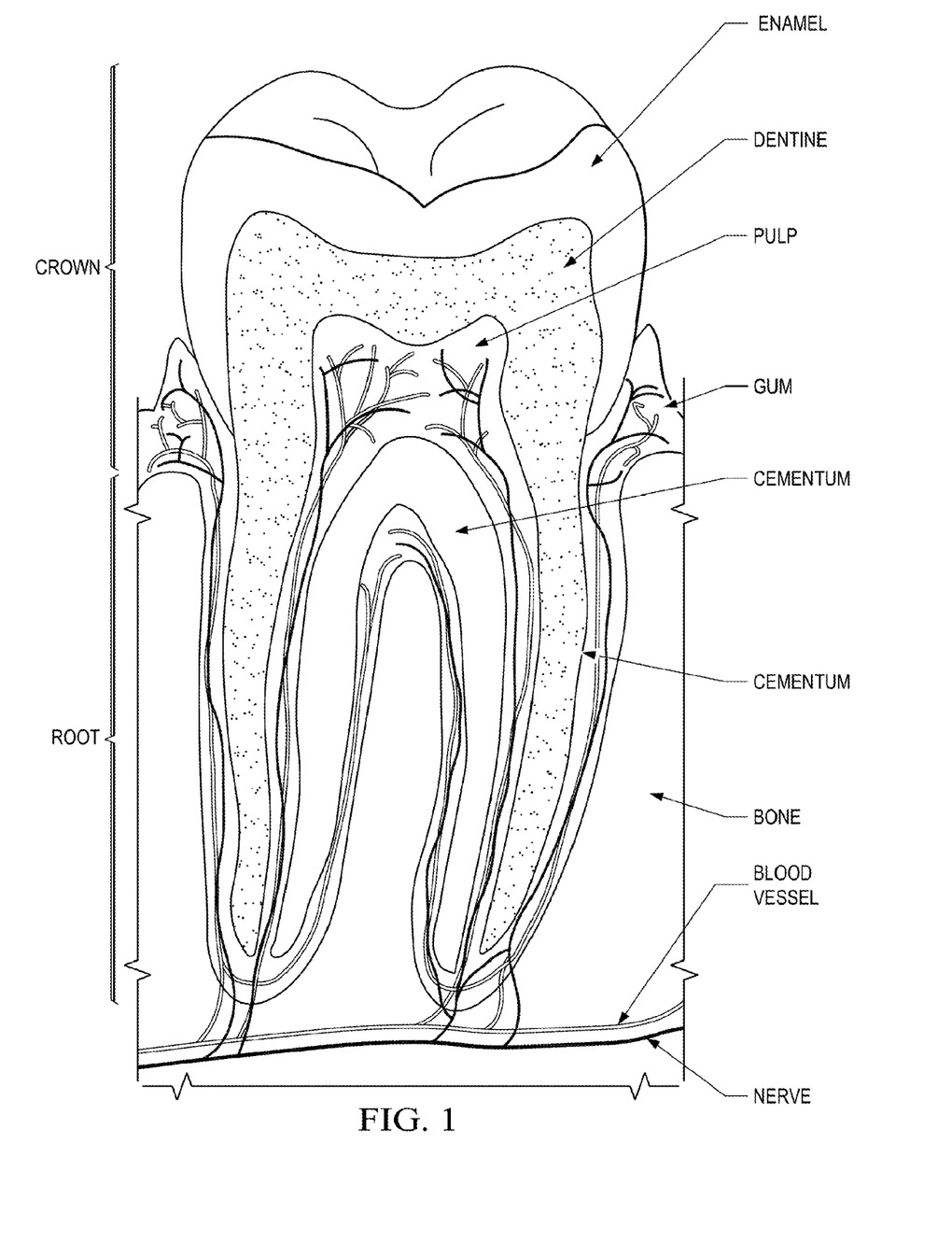
FIG. 1 is a cross section of tooth showing the various structures.

Tooth enamel, along with dentin, cementum, and dental pulp (see FIG. 1) is one of the four major tissues that make up the tooth. It is the hardest and most highly mineralized substance in the human body. Ninety-six percent of enamel consists of mineral, with water and organic material composing the rest. The primary mineral is hydroxyapatite, which is a crystalline calcium phosphate.

The high mineral content of enamel, which makes this tissue the hardest in the human body, also makes it susceptible to a demineralization process which often occurs as dental caries, otherwise known as cavities. Demineralization occurs for several reasons, but the most important cause of tooth decay is the ingestion of fermentable carbohydrates.

Tooth cavities occur when acids dissolve tooth enamel:

$$Ca_{10}(PO_4)_6(OH)_2(s)+8H^+(aq) \rightarrow 10Ca^{2+}(aq)+6HPO_4^{2-}(aq)+2H_2O(l)$$

Sugars from candies, soft drinks, and even fruit juices play a significant role in tooth decay, and consequently in enamel destruction. The mouth contains a great number and variety of bacteria, and when sucrose, the most common of sugars, coats the surface of the mouth, some intraoral bacteria interact with it and form lactic acid, which decreases the pH in the mouth. Then, the hydroxylapatite crystals of enamel demineralize, allowing for greater bacterial invasion deeper into the tooth. Demineralization involves the loss of calcium, phosphate, and carbonate. These cycles of demineralization and remineralization continue throughout the lifetime of the tooth.

Figure 2:
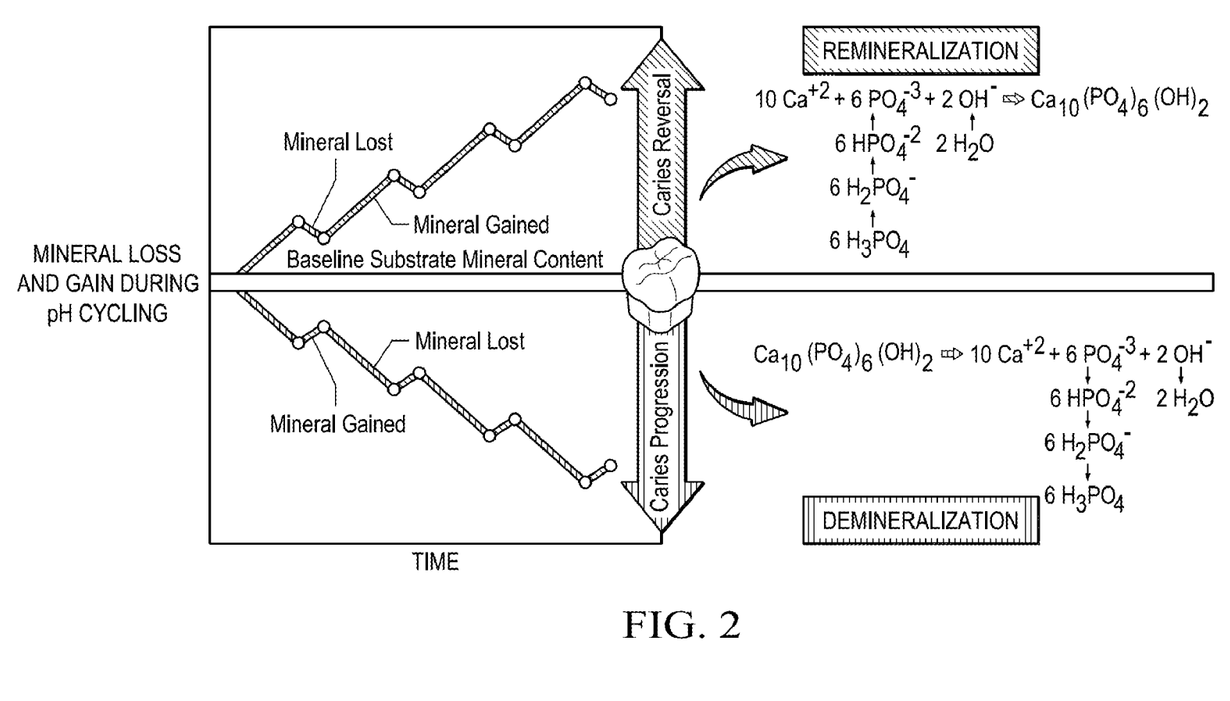
FIG. 2 shows the mineralization and demineralization cycle of enamel.

Fluoride works to control early dental caries in several ways. Fluoride concentrated in plaque and saliva inhibits the demineralization of sound enamel and enhances the remineralization (i.e., recovery) of demineralized enamel. As cariogenic bacteria metabolize carbohydrates and produce acid, fluoride is released from dental plaque in response to lowered pH at the tooth-plaque interface. The released fluoride and the fluoride present in saliva are then taken up, along with calcium and phosphate, by demineralized enamel to establish an improved enamel crystal structure (FIG. 2). This improved structure is more acid resistant and contains more fluoride and less carbonate. Fluoride is more readily taken up by demineralized enamel than by sound enamel.

Figure 3:
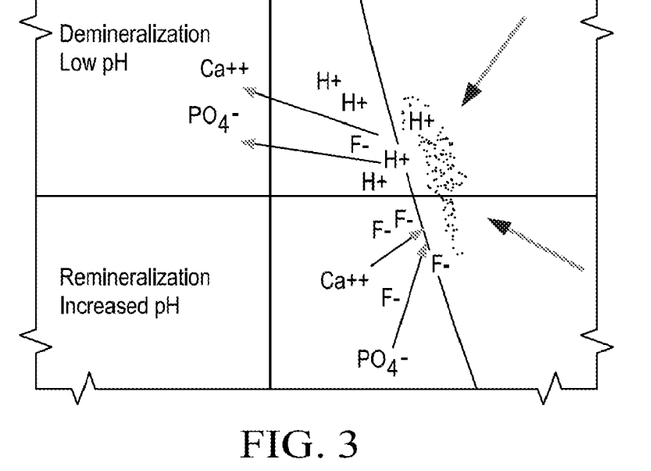
FIG. 3 shows mineralization aided by fluoride.

Fluoride also inhibits dental caries by affecting the activity of cariogenic bacteria. As fluoride concentrates in dental plaque, it inhibits the process by which cariogenic bacteria metabolize carbohydrates to produce acid and affects bacterial production of adhesive polysaccharides (FIG. 3).

The scientific support for remineralization by fluoride is well established. Wu (2012), for example, used enamel specimens in an in vivo model of demineralization and remineralization wherein specimens were observed by stereomicroscope and scanning electron microscope and compared in surface microhardness value. These workers found a distinct difference in micro-morphologic appearance on fluoride enamel surface. Artificial caries of fluoride enamel showed a relatively complete surface, the surface microhardness after demineralization and remineralization in fluoride group was higher than non-fluoride group (P<0.05). They concluded that fluorinated enamel can enhance cariostatic potential and remineralization capacity of dental enamel.

Similarly, Austina (2010) investigated the effect of an aqueous sodium fluoride solution of increasing concentration on erosion and attrition of enamel and dentine in vitro. Enamel and dentine sections from caries-free human third molars were polished flat and taped (exposing a 3 mm×3 mm area). All specimens were subjected to 5, 10 and 15 cycles of experimental wear with artificial saliva, erosion and attrition. Following tape removal, step height (SH) in μm was measured using optical profilometry. These scientists found that 5000 ppm and 19,000 ppm sodium fluoride solutions had a protective effect on erosive and attritional enamel tooth wear in vitro, however no other groups showed significant differences. They concluded that the more intensive the fluoride regime, the more protection was afforded to enamel from attrition and erosion. However, no such protective effect was demonstrated for dentine.

Thus, the evidence fully supports the value of applying fluoride gel or other product containing a high concentration of fluoride to the teeth to leave a temporary layer of calcium fluoride-like material on the enamel surface.

Of course, too much fluoride can be harmful as well, especially in younger children whose teeth are still developing. A NCHS Data Brief No. 53 published in 2010 established that while tooth decay decreases with fluoridating water, fluorosis increases, especially in children. Dental fluorosis is defined as a change in the mineralization of the dental hard tissues (enamel, dentin, and cementum) caused by long-term ingestion (eating and drinking) of fluoride during the period of tooth development prior to eruption into the mouth (first 8 years of life for most permanent teeth excluding third molars). Once the tooth erupts, dental fluorosis refers to a range of visually detectable changes in enamel. Changes range from barely visible lacy white markings in milder cases to converged opaque areas and pitting of the teeth in severe forms. After eruption the pitted areas can become stained yellow to dark brown.

Fluoride containing gels and rinses are available for use in managing dental health, but nothing specifically developed for orthodontic use has yet been developed.

OrthoAccel has developed a revolutionary orthodontic treatment device that can be used in conjunction with e.g., braces, retainers, positioners, fixed class II correctors and clear positioners. US2008227046 et seq, and US20120322018 describe a vibrating device that can reduce orthodontic treatment time by as much as 30-50%. This device, known as AcceleDent®, includes a detachable bite plate allowing for contact with occlusal and facial and/or lingual teeth (maxillary and mandibular). The bite plate is reversibly coupled to an extraoral housing containing a rechargeable battery coupled to a vibrator coupled to a processor that can record and transmit device usage or compliance data.

In additional to cyclic forces (aka microvibration), OrthoAccel is experimenting with other treatment modalities that can further speed orthodontic remodeling, including low energy IR laser dental devices (61/624,242, filed Apr. 13, 2012) and electric micropulse based devices (61/673, 236, filed Jul. 18, 2012). Each of these new devices can be made with the same or similar detachable bite plates provided with the AcceleDent® device.

Demineralization is a particular problem that often accompanies orthodontic treatment. People with orthodontic braces often have trouble properly brushing their teeth due to brace bulk and the result is a build-up of plaque near the braces. The acids in plaque can severely harm tooth enamel and eventually cause cavities, but the first evidence of this type of tooth decay is the white decalcified enamel spot or lesion that suddenly becomes apparent when braces are removed.

It would thus be particularly beneficial if the AcceleDent® could provide the user with fluoride during use, thus helping to avoid the demineralization that often occurs with brace usage. Of course, any of the existing fluoride gels or foams could be applied to the bite plate before use, but such liquids tend to be messy, thus discouraging their use. Instead, a device that releases fluoride only in a wet oral environment would eliminate both the mess and the need to apply gel. Further, since the device is only indicated for 20 minutes usage a day, it also addresses the concerns over excess fluoride, and presents less significant FDA hurdles in approval.

Thus, what is needed in the art is a bite plate, designed for orthodontic use, that steadily releases beneficial fluoride ions during use.

SUMMARY OF THE DISCLOSURE

The disclosure generally relates to bite plates used with orthodontic remodeling devices and which release fluoride ions during use. The bite plate can also release other agents, such as antibacterial agents like silver ions, whitening agents, and the like, but the main focus herein is on fluoride containing compounds that can inhibit caries and remineralize enamel.

Although, specifically contemplating use with orthodontic appliances such as the AcceleDent®, such materials could also be used with other orthodontic appliances, such as tooth positioners and/or clear aligners, although since these are worn about 22 hours per day, the release rate for the fluoride will have to be adjusted accordingly.

Preferably, the fluoride material is an FDA approved or cleared material. For example, 21 CFR Sec. 355.10 allows dentrifices with 0.188-0.254% sodium fluoride or 0.351-0.474% stannous fluoride. Rinses are allowed with acidulated phosphate fluoride derived from sodium fluoride acidulated with a mixture of sodium phosphate, monobasic, and phosphoric acid to a level of 0.1 molar phosphate ion and a pH of 3.0 to 4.5 and which yields an effective fluoride ion concentration of 0.02-0.05 percent. Other formulations include sodium monofluorophosphate—dentifrices containing 850 to 1,150 ppm theoretical total fluorine in a gel or paste dosage form or dentifrices containing 1,500 ppm theoretical total fluorine in a gel or paste dosage form or sodium monofluorophosphate 1.153 percent with an available fluoride ion concentration (consisting of $PO_3 F^{-2}$ and $F^-$ combined)≥1,275 ppm.

Alternatively, a silver fluoride compound can be used, although none are yet approved. About a hundred binary, ternary, and quaternary silver fluorides are known, among them are six binary species: $Ag_2F$, $AgF$, $AgF_2$, $Ag_2F_5$, $Ag_3F_8$, and $AgF_3$. Such compounds can provide both antimicrobial and remineralizing effects, and can be particularly beneficial.

Rosenblatt (2009), for example performed a literature review of 99 human clinical trials, showing silver diamine fluoride (SDF) was much more effective at arresting caries than fluoride varnish (see Table 1). Of course, silver diamine fluoride presents additional regulatory hurdles, but providing the chemical on a device used for 20 minutes daily, will alleviate some of the regulatory concerns that occur with a gel that can be swallowed, or with appliances that are worn 24/7 resulting in much greater overall exposure.

TABLE 1

|  | Caries Arrest | Caries Prevention |
| --- | --- | --- |
| silver diamine fluoride | 96.1% | 70.3% |
| fluoride varnish | 21.3% | 55.7% |

In more detail, the invention includes one or more of the following embodiments in any combination:

A fluoride-releasing bite plate. Fluoride-releasing tooth positioners or aligners are also provided.

The bite plate can comprise a polymer that releases fluoride, or alternatively the bite plate can be coated with a polymer or glass ionosphere coating that releases fluoride. As another alternative, strips of fluoride-releasing material can be applied to the tooth contacting surfaces of the bite plate. As yet another alternative, a removable insert comprising a polymer that releases fluoride can be introduced into the bite plate.

In one embodiment, a fluoride-releasing bite plate comprises: a) an intraoral bite plate comprising a fluoride-releasing material; b) said intraoral bite plate having a substantially U-shaped surface for contacting an occlusal surface of teeth; c) said U-shaped bite plate having an outside edge having upper and lower rims to contact an upper and lower facial surfaces of teeth and gums; d) said U-shaped bite plate having an inside edge having optional upper and lower rims to contact at least a portion of an upper and lower lingual surfaces of teeth and gums; and e) said U-shaped bite plate also having a connector for reversibly coupling said bite plate to a separate extraoral orthodontic remodeling device.

Preferably, the orthodontic remodeling device vibrates at a single frequency between 1-400 Hz, or at 30 Hz, and at 0.1-5 N or 0.2 N. Also, the device is held in place during usage only by teeth clamping on the bite plate, and lacks other head and/or neck attachment means. Such a device when used daily for 20 min can reduce orthodontic remodeling time up to 50% as compared to the use of orthodontic appliances alone without said daily vibration. "Daily" in this context means at least 67% compliance, but preferably 75, 80, 85, 90% compliance or better.

The fluoride-releasing compound can be any herein described, but is preferably a stannous fluoride or sodium fluoride or silver fluoride, or can be any other suitable fluoride containing compound. It can also be combined with other active agents, such as phosphates or antibacterial agents, drugs and the like.

In one example, the fluoride-releasing material comprises micronized fluoride containing filler in a polymeric substrate. Polymers can be any biocompatible medical grade polymer, including silicones, polyurethanes, and the like. Alternatively, the polymeric material can include a polymer selected from the group consisting of methacrylate polymers, methacrylate copolymers, and mixtures thereof; a monomer selected from the group consisting of monomeric heterocyclic methacrylic esters, C3-C4 methacrylic esters, and mixtures thereof; and 0.5-2% non-toxic, biologically acceptable metal fluoride; wherein the ratio of the polymer to the monomer is from 1.25:1 to 1.75:1 by weight.

In preferred embodiments, the said bite plate is medical grade polymeric silicone and stannous fluoride, sodium fluoride, or any of the silver fluoride agents named herein.

In another embodiment, the fluoride-releasing material also comprises a colorant or a sustained-release matrix that changes or decreases in color intensity over time and use. The colorant (i.e. a non-toxic dye or pigment) will serve as an indicator that informs the user when its time to replace the fluoride-releasing material.

The non-toxic dye or pigment can be water-soluble such that it is released on contact with saliva. Also, it can be located in the outer layers of the fluoride-releasing material such that an amount will be released during each use. The amount of colorant used can be augmented to match the expected duration of the fluoride in the fluoride-releasing material.

Alternatively, a sustained-release matrix containing a support resin, a water-soluble substance (preferable a water-soluble polymer), and a non-toxic dye can be used. The support resin can be any of the fluoride-releasing polymers described above. Also, the fluoride-releasing polymer described above can have an 'outer layer' comprising the sustained-release matrix with less fluoride-releasing polymer in the support resin than that found in the material.

The water-soluble substance is preferably polymers such as starches, polyvinyl alcohols, polyethylene oxides, hydroxyalkyl starches, hydroxyethyl and hydroxypropyl celluloses, and gelatins. On contact with saliva, the water-soluble substance will dissolve, thus releasing the non-toxic dye or pigment.

In one embodiment, the support resin or the fluoride-releasing material can also contain a colorant that is different from the non-toxic dye in the sustained-release matrix. This can serve as a template for a different color, or shade of color, than the colorant in the outer layer.

In another embodiment, a fluoride-releasing bite plate comprises: a) an intraoral bite plate having a removable core comprising a fluoride-releasing material; b) said intraoral bite plate having a substantially U-shaped surface for contacting an occlusal surface of teeth; c) said U-shaped bite plate having an outside edge having upper and lower rims to contact an upper and lower facial surfaces of teeth and gums; d) said U-shaped bite plate having an inside edge having optional upper and lower rims to contact at least a portion of an upper and lower lingual surfaces of teeth and gums; e) said removable core having a substantially U-shaped, flat surface that fits snugly between said upper and lower rims of the bite plate; f) said U-shape bite plate having a tab for reversibly coupling said bite plate to said removable core; and g) said U-shaped bite plate also having a connector for reversibly coupling said bite plate to a separate extraoral orthodontic remodeling device.

In fluoride-releasing core embodiments, the portion of the bite plate overlaying the core (if any) must be such as to allow free passage of fluoride, and thus may have holes or be a porous material.

In yet another embodiment, a fluoride-releasing bite plate comprises: a) an intraoral bite plate having a core comprising a fluoride-releasing material; b) said intraoral bite plate having a substantially U-shaped surface for contacting an occlusal surface of teeth; c) said U-shaped bite plate having an outside edge having upper and lower rims to contact an upper and lower facial surfaces of teeth and gums; d) said U-shaped bite plate having an inside edge having optional upper and lower rims to contact at least a portion of an upper and lower lingual surfaces of teeth and gums; e) said core having a substantially U-shaped, flat surface; and f) said U-shaped bite plate also having a connector for reversibly coupling said bite plate to a separate extraoral orthodontic remodeling device.

DESCRIPTION OF FIGURES

FIG. 4 shows a perspective view of a bite plate from two angles, showing the flat U-shaped base, and upper and lower lingual and facials rims, as well as the stem, which fits into a mating socket on the extraoral housing (not shown). FIG. 4A shows the stem facing away, whereas

FIG. 5 shows the core of the bite plate from two angles over which is molded a biocompatible overlay having the rims and desired final shape. FIG. 5A shows the stem facing away, whereas

FIG. 8 shows the removable fluoride-releasing material according to one embodiment of the present invention.

FIG. 9A-C shows the removable fluoride-releasing material according to a second embodiment of the present invention.

DETAILED DESCRIPTION

The fluoride compound can be intimately admixed with the polymer that forms the bite plate. Alternatively, it is possible to apply the fluoride compound by spraying or otherwise coating a thermoplastic resin bite plate with the compound and drying, if necessary, prior to packaging. As yet a third alternative, a strip of fluoride-loaded material can be applied to the tooth facing surfaces. As yet another alternative, the bite plate can comprise a removable fluoride-releasing core that is replaced after a number of uses, possibly indicated by color change. As yet another alternative, the bite plate can comprise a removable fluoride-releasing core that is replaced after each use. Single use removable fluoride-releasing core can be a simple absorbent pad saturated with a solution containing fluoride, then dried and packaged and sold for use.

Fluoride-releasing polymers and glasses are already known, and their effectiveness can be evaluated using double-distilled water, artificial saliva, and lactic acid. Briefly, the specimen is placed in the solution for a period of time, and samples assessed every 10-30 minutes for fluoride content. The experiment can be repeated under vibratory conditions as well, simulating the 0.2 Newton and 30 Hz vibration of the AcceleDent® device. It is expected that the pH of the environment will strongly affect the fluoride release from the materials, and vibration may also allow some increase in the rate of release, although the release in water and artificial saliva is expected to show no significant difference. A variety of fluoride sources, concentrations and mill sizes will be tested in silicone or other polymers according to the above method.

Antimicrobial action can also be tested, for e.g., silver fluoride-releasing polymers at least initially using ASTM E2180—Standard Method for Determining the Activity of Incorporated Antimicrobial Agent(s) in Polymeric or Hydrophobic Material.

As known, many polymers that release fluoride or silver are already known.

U.S. Pat. No. 5,718,924, for example, describes a fluoride-releasing dental composition comprising a polymer, a monomer and a metal fluoride. The polymer may be an acrylate polymer, a methacrylate polymer or a copolymer thereof. The monomer may be a monomeric heterocyclic acrylic ester, a monomeric heterocyclic methacrylic ester, a C3-C16 alkyl acrylic ester or a C3-C16 methacrylic ester. The metal fluoride is a nontoxic, biologically acceptable metal fluoride. In certain embodiments, the metal fluoride is sodium fluoride. The metal fluoride may comprise from approximately 0.1% to approximately 2% of the composition by weight.

U.S. Pat. No. 5,198,220 describes a composition that can be a liquid, paste or solid, depending on the rations of ingredients. Copolymer of lactide and glycolide are blended with propylene carbonate and active agent, such as fluoride. Further, since such polymeric materials do undergo slow degradation via hydrolysis, the drug continues to be released in a sustained manner from such compositions.

U.S. Pat. No. 4,044,762 describes a composite wherein the resin melts at a lower temperature than a fluoride containing powder, such that the resin can be melted, blended with the powder, and resolidified in a desired shape. The powders will solubilize in the mouth and leach out, releasing fluoride. One example describes 98 parts by weight of thermoplastic resin beads to two parts by weight of sodium fluoride, stannous fluoride or sodium fluorosilicate powder. The mixture is heated and mixed until the resin becomes sufficiently molten for molding. The molding temperature of the resin is well below the melting temperature of the powdered fluoride compound constituent of the composition. The composition is then injected into a mold of the desired shape to form the bite plate.

US20120285574 describes an antimicrobial mouth-guard. In this application, fill material was used with a polymer, wherein the fill included antimicrobial micronized or sub-micron-sized particles of silver or other metals or metal complexes known to exhibit anti-bacterial or anti-microbial activity incorporated into the resin concentrate prior to molding of the dental appliance. The resin concentrate is an elastomeric polymer composition comprising liquid silicone rubbers, other silicone elastomers, fluorinated elastomers, thermoplastic elastomers, polyurethanes, composites of polyvinyl chloride, polyethylene, polypropylene and copolymers of polyethylene and polypropylene, composites including C60 and wherein the elastomeric polymer composition includes micronized or submicron sized particles of metals or metal complexes and wherein the particles may be added before or during a molding process such that the mouthguard and/or divers mouthpiece will permit controlled antimicrobial action from the dental appliance, mouthguard and/or divers mouthpiece to the mouth of the user.

Micronized silver (3.5 g/mouthpiece) was mixed into the silicone rubber (amount not given but average weight of a mouthguard is about 10 grams), and antimicrobial activity tested with ASTM E2180, using test organisms utilized were *Staphylococcus aureus* ATCC 6538 and *Pseudomonas aeruginosa* ATCC 15442. Although poor silver distribution was observed, it was clear that the micronized silver had an antimicrobial effect. Thus, e.g., 10-40% silver diamine fluoride fill can be blended with the polymer of bite plate, e.g., silicone, and provide both antimicrobial and remineralizing effect.

U.S. Pat. No. 6,009,589 describes a silver containing toothbrush, wherein bristles are held on the brush by e.g., a layer of pure silver or alloy of silver and copper with a silver content of between 90% and 97%, approximately, and a copper content of between 10% and 3%, approximately, or alternatively, of an alloy of silver and titanium with a silver content of 70%, approximately, and a titanium content of 30%, approximately. In the moist environment of the mouth, a metal coating of the silver coating with a thickness of between 5 and 50 micrometers, in particular 5 to 20 micrometers, the toothbrush will release silver with antibacterial effect. This toothbrush is 501K cleared as the SILVER CARE ANTIBACTERIAL TOOTHBRUSH (K102871), suggesting that such an approach will engender fewer regulatory hurdles.

As another option, de Francisco (2012) describes ethylcellulose microparticles containing fluoride ("EM") that were prepared by emulsification of ethyl acetate dispersion containing polymer and fluoride sources ("FS") (ethylcellulose:FS ratio of 1:0.25 wt/wt) with aqueous external phase containing polysorbate 80 (0.8% vol/vol) using the volume ratio (organic:aqueous) of 1:5. The organic solvent was evaporated; microparticles were collected by centrifuging, washed with deionized water and freeze-dried. Gelatin microparticles containing FS ("GM") were obtained by dispersion of the natural polymer in water, adding FS (6:1 wt/wt) and 20% (wt/wt) of mannitol. The release profile of fluoride ions from microparticles was shown to be a modified, fitted first order release and guided by Fickian diffusion.

Baturina (2010) describes a polyethylene co-vinyl acetate (PEVA) that was used as the model elastomer (0.4 g NaF/4.2 g PEVA) in blended and dip coated samples. Dip coating provided fluoride release at a therapeutically effective rate and profile.

Lin (2003) describes a drug loaded ethylene vinyl acetate copolymer (EVA) made by dissolving EVA and the drug in a ratio of 40:1 in 70 ml of dichloromethane at 38 degrees C. for 6 h. Thin square films of 3×3 cm$^2$ with a thickness of 1 mm were cut from the dry sheet obtained by solvent evaporation technique. Drug loaded samples were extracted for a minimum of 14 days in 10 ml medium (double distilled water or water/ethanol (4:1)) that was replaced daily. Spectral measurements were made to follow changes in optical densities (OD) during release kinetics. Analysis of variance of the data revealed that significantly enhanced rates were observed at the higher temperature (37° C.) and when extracting medium was changed to water/ethanol (4:1)). Such polymer could easily be loaded, e.g., with a fluoride-releasing compound.

Lynch (2012) described "Melt-derived multi-component bioactive glasses ("BG") ($SiO_2$—$P_2O_5$—CaO—$CaF_2$—SrO—$SrF_2$—ZnO—$Na_2O$—$K_2O$ with increasing $CaF_2$+$SrF_2$ content (0-32.7 mol %)." When the BG was used to treat dentin discs, the fluoride containing BG formed apatite from as early as 6 hours, while the fluoride-free control did not form apatite within 7 days. The authors concluded "Fluoride significantly improved apatite formation of the BG, allowing for treatment of [Dentin hypersensitivity] by occlusion of dentinal tubules. The BG also released therapeutically active ions, such as strontium and fluoride for caries prevention, zinc for bactericidal properties and potassium, which is used as a desensitizing agent in dentifrices."

Arbabzadeh-Zavareh (2012) describes glass ionospheres that can be recharged with fluoride on exposure to fluoride. Products containing glass ionospheres are already available. Ultraseal XT Plus clear sealant (Ultradent Products, South Jordon, Utah) or OpalSeal, each contain glass ionospheres that recharge with fluoride, e.g. from toothpaste during brushing. These materials could thus be easily applied to a bite plate during manufacturing as a coating material or core, and they would leach fluoride during use. The ionospheres can be recharged by soaking in e.g., a disinfecting, fluoride containing solution, or the bite plates can be disposable, used for only a short period of time.

As discussed above, the bite plates herein provided comprise a fluoride-releasing material. The structure of the bite plates in preferred embodiments, is detailed next.

Figure 4A:
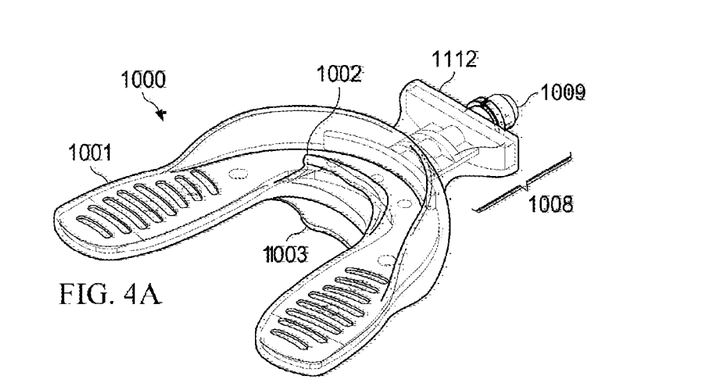
Figure 4B:
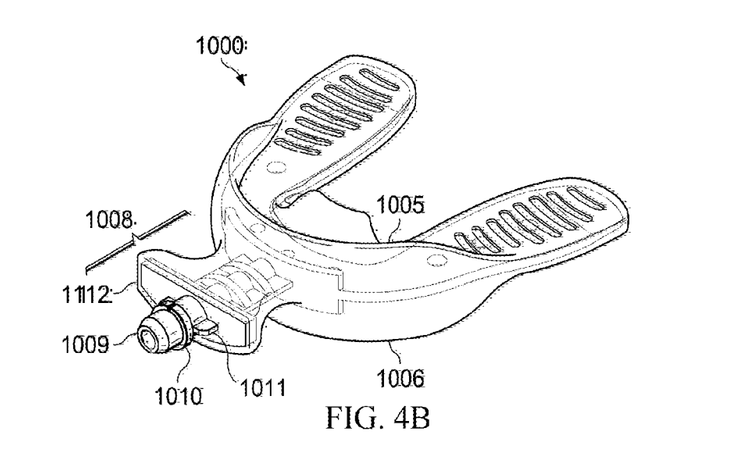
FIG. 4B shows the stem facing viewer.

FIG. 4A-B shows an improved bite plate (1000), having generally U-shaped base (1001) that contacts occlusal surfaces of the teeth, the base having front and back edges, one or both edges having a rim to contact the facial and lingual surfaces of upper and lower teeth and/or gums. Thus, upper lingual rim (1002), lower lingual rim (1003), upper facial rim (1005) and lower facial rim (1006) are shown. In this instance, the lingual rims contact only the incisors and/or canines, but not the molars. However, the rims can be varied in length to contact all, or a portion, of the teeth. It is preferred that at least one rim contact each tooth, except for specially designed bite plates made to correct extreme abnormalities.

Also shown in FIG. 4A-B is the stem (1008), which is the portion of the bite plate (1000) that mates with a corresponding socket in the extraoral housing (not shown here). In more detail, a cylindrical shaft (1009) is shown, having a groove (see FIGS. 5-6) into which a jump ring (1010) fits, and mates with a corresponding depression in the socket. Optional flare (1112) is also shown, and is configured to provide an appropriate surface so that the user can push the stem into the socket.

The thickness of the biocompatible overlay material can be adjusted to compensate for various patient bite configurations (open, deep, flat), as detailed in US2010055634, incorporated by reference herein. However, in most instances a bite plate that is slightly thinner at the distal end than the mesial end will accommodate the hinged nature of the temporomandibular joint and facial skeleton.

Thus, if a U-shaped bite plate has two back ends that can contact one or more distal or posterior teeth, and a front end that can contact one or more mesial or anterior teeth, and a thickness E, wherein said thickness E is 2-10 mm, the bite plate can be in one of three configurations:

a) thickness E does not substantially vary from said front end to said back ends;

b) thickness E increases from E at said front end to E plus 0.5-10 mm at said back ends;

c) thickness E increases from E at said back end to E plus 0.5-10 mm towards said front end.

We have shown the stem on the bite plate, but the bite plate may contain the socket, and the extraoral component may have the stem. Further, we have shown a cylindrical shaft with jump ring circumnavigating the shaft (a cylindrical type snap fit), as one example of a reversible coupling mechanism, but any reversible coupling mechanism could be employed, including a cantilevered beam snap fit, a spherical snap-fit, depressible push pins and sockets, a threadable screw fit, and the like.

Figure 5A:
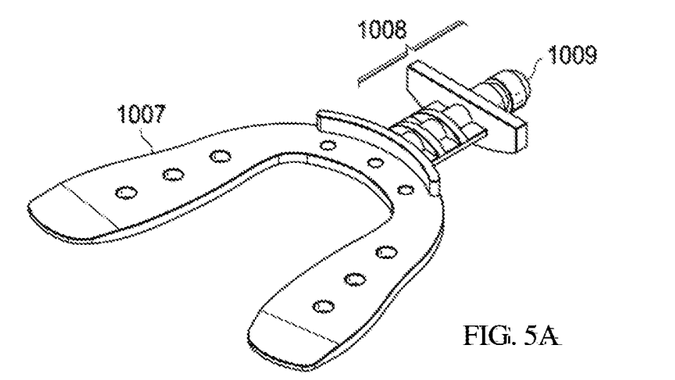
Figure 5B:
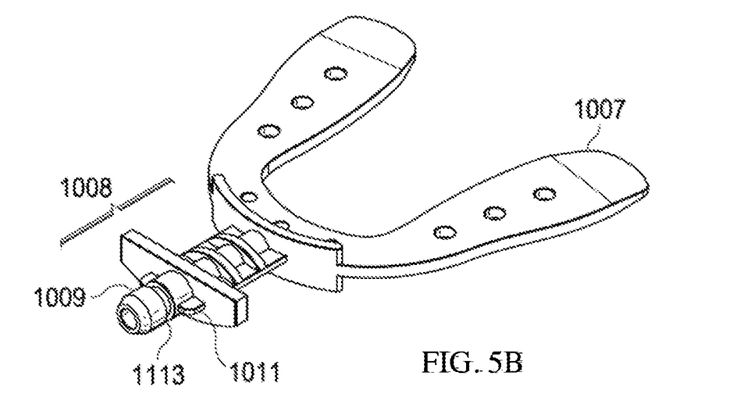
FIG. 5B shows the stem facing viewer.

FIG. 5A-B shows the core (1007) of one bite plate, typically made from a resin, metal or ceramic having a harder durometer than the outer surface, and providing sufficient rigidity to the stem (1008) so as to allow it to lockingly fit into the socket. Cylindrical shaft (1009) has a groove (1113), into which jump ring (1010) fits (see FIG. 6). Also seen are locking pins (1011). Generally, plastics of at least 40 Shore D are used for the core, but metals or ceramics could also be used. A coating is provided over this core, and provides the final shape of the bite plate, as shown in e.g., FIG. 7. Such coating should be a biocompatible soft polymer of 40-70 Shore A, and particularly preferred is a medical grade, clear silicone.

Figure 6:
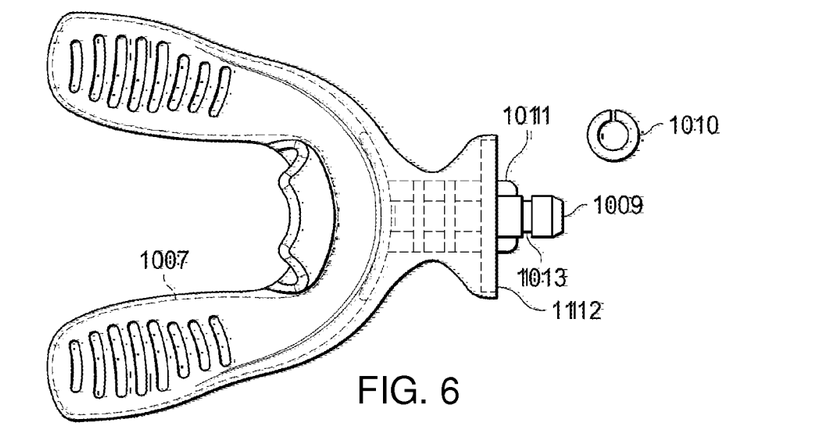
FIG. 6 shows a top view of the bite plate, more clearly illustrating the stem, flare, pins, cylindrical shaft and groove, into which fits the jump ring that mates with a corresponding recess in the socket (not shown).

FIG. 6 shows a top plan view of the bite plate, more clearly illustrating the core (1007), shaft (1009), flare (1112), pins (1011) and jump ring (1010), as well as the other edge of the overcoat, which provides the actual shape of the bite plate.

Figure 7:
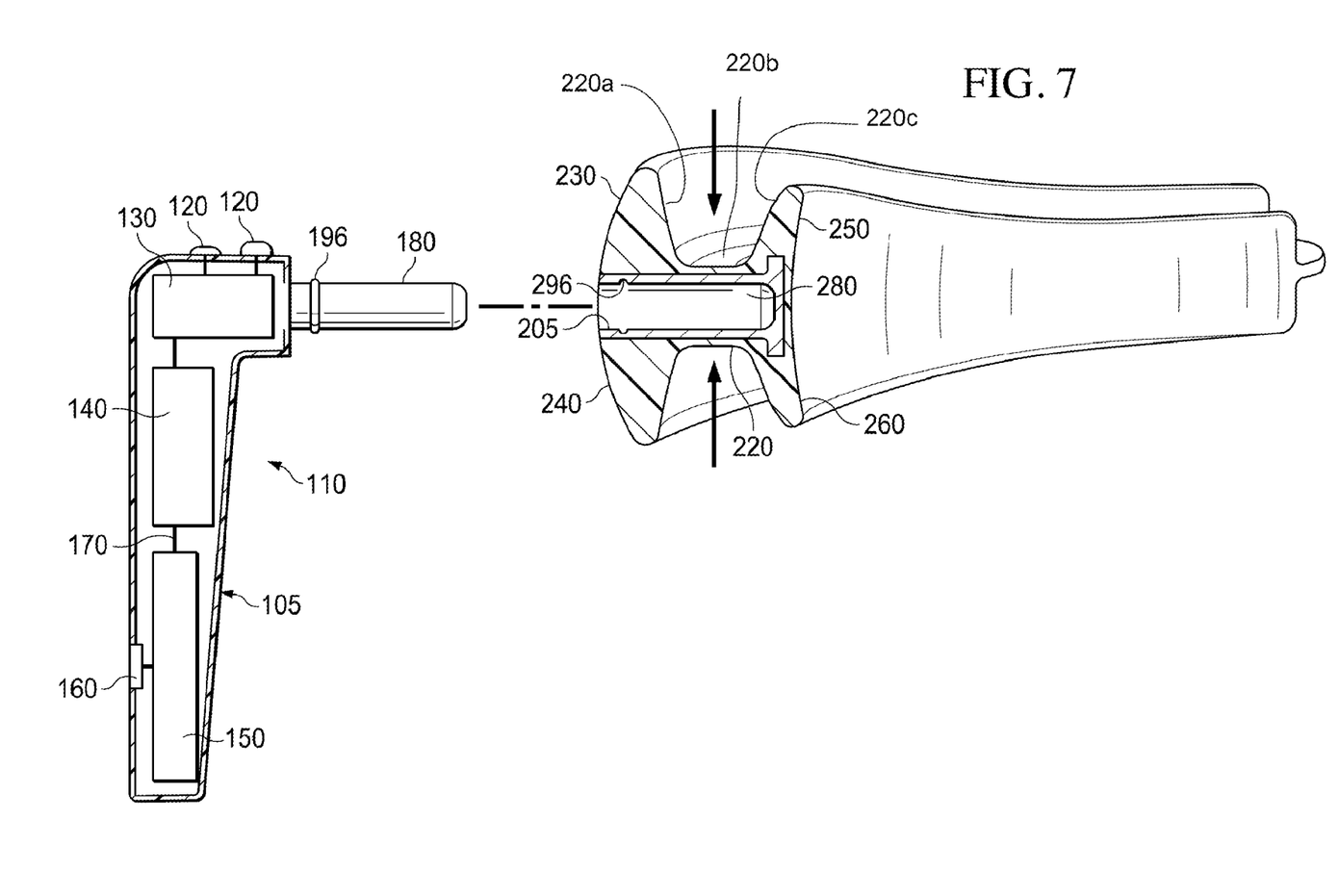
FIG. 7 shows a complete device with extraoral activator providing e.g., vibration, IR light and/or electric micro-pulses, as well as bite plate.

Another exemplary structure is more clearly illustrated in FIG. 7, which is a cross section of the vibratory device (110) and half of a bite plate (220). The vibratory device (110) has a housing (105) containing all components, except the stem (180), which protrudes therefrom. Preferably, housing (105) is water resistant or even more preferred it is waterproof or hermetically sealed. The housing contains battery (130), preferably a rechargeable battery and can have an optional charging port (not shown). A source of activator (140), which is preferably a vibrating offset motor or piezoelectric motor, is shown schematically as a simple box. Activator (140) could also represent another treatment modality such as IR light or electric micropulses. Processor (150) captures usage data, and may control the activator (140). Data is transmitted to a server or computer or the internet via data port or USB (160). Connections or wires (170) are shown in simple form only and not intended to convey actual wiring connections, as are on/off switches (120). Stem (180) is shown here with depressions (190), which can circumnavigate the stem in one embodiment, but many variations of snap fitting and other connectors are possible.

Bite plate (220) has an optional hard inner core that forms the socket (280) and can be any suitable shape. A circle spring (290) fits into depressions (190) on stem (180) and the tooth positioner thus removably snap fits onto the extraoral vibratory device. The bite plate has the labial, lingual edges and occlusal surfaces as already described. Thus, (220) contacts teeth surfaces, including facial (220a), occlusal (220b), and lingual (220c) surfaces, and these surface at least should be fluoride-releasing. Edges (250) and (260) provide the structure needed to provide the lingual tooth contacting surfaces, while edges (230) and (240) allow for contact with facial teeth surfaces. These various surfaces (220) are simply drawn herein, but can also shaped to more closely follow a patient's teeth. Preferably, these edges are made of a resilient material of durometer at least 70 Shore A, most preferred is a biocompatible or medical grade clear silicone.

Figure 8A:
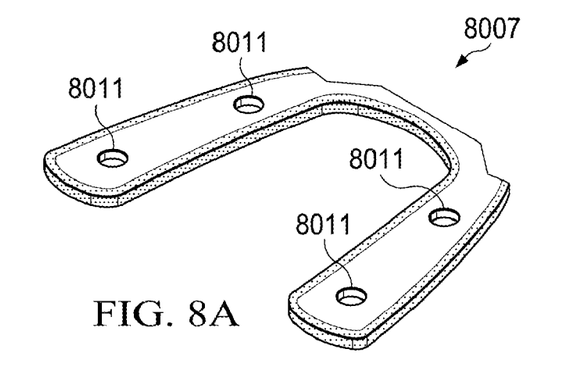
FIG. 8A displays a top view of a removable core comprising fluoride-releasing material.
Figure 8B:
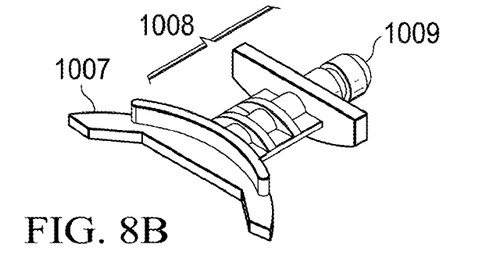
FIG. 8B shows a truncated version of the core from FIGS. 5A-B and 6 with a notched edge.
Figure 8C:
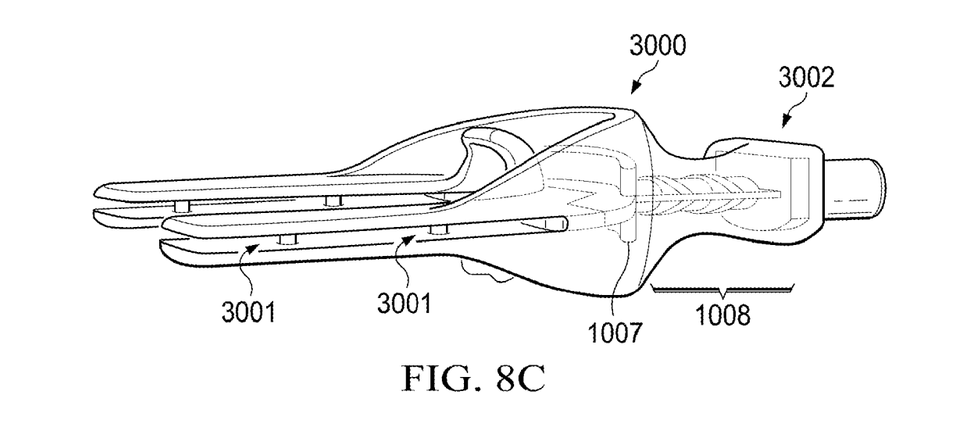
FIG. 8C displays a molded bite plate coating with the core from FIG. 8B.

FIG. 8A-E displays one embodiment of the removable fluoride-releasing core for use with the bite plate and the insertion of the fluoride-releasing core into the molded bite plate coating. FIG. 8A displays a generally U-shaped removable core with a fluoride-releasing material (8007). The U-shaped removable core can include a colorant or sustained-release matrix that changes or decreases in color intensity over time and use. This U-shaped removable fluoride-releasing core fits snuggly in a molded bite piece coating (3000), as seen in FIG. 8C. The removable core also has holes (8011) for reversible securing the core to the molded bite piece coating. Additionally, the mid-line region of the removable core has a notched section that is complementary to a notched portion of the core (1007) in FIG. 8B. Any shape can be used for this region as long as the juncture between the two pieces fit smoothly, much like puzzle pieces, with the core in FIG. 8B.

FIG. 8B displays a truncated version of the bite plate core (1007) in FIGS. 5 and 6. This truncated version fits into the bite plate coating (3000) and the stem (1008) and cylindrical shaft (1009) fit into a mating socket on the extraoral housing (not shown). It is truncated and notched to allow for alignment with the removable fluoride-releasing material core (8007).

FIG. 8C displays the molded bite piece coating (3000) that provides the final shape of the bite plate and the tab (3001) for reversible binding the core. The truncated version of the bite plate core (1007) is securely placed such that the stem of the bite plate (1008) is in the stem (3002) of the coating (3000). The molded bite piece coating may optionally be very porous or have large cutouts along the upper and lower rims to facilitate fluoride transfer.

Figure 8D:
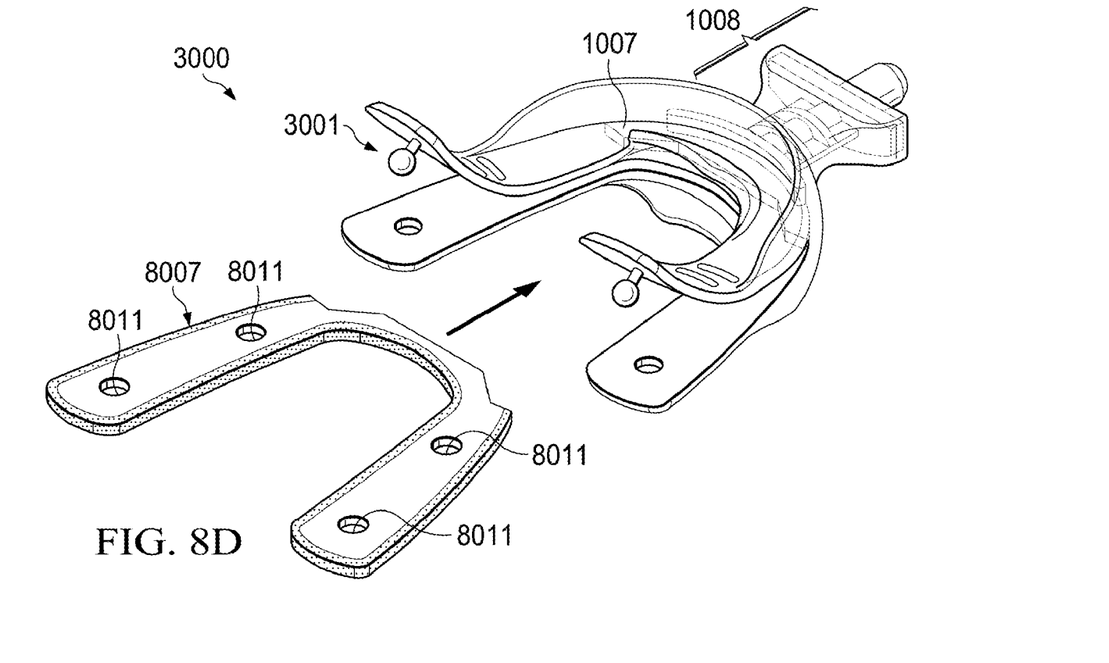
FIG. 8D shows the molded bite plate coating opened to receive the removable fluoride-releasing core from FIG. 8A.
Figure 8E:
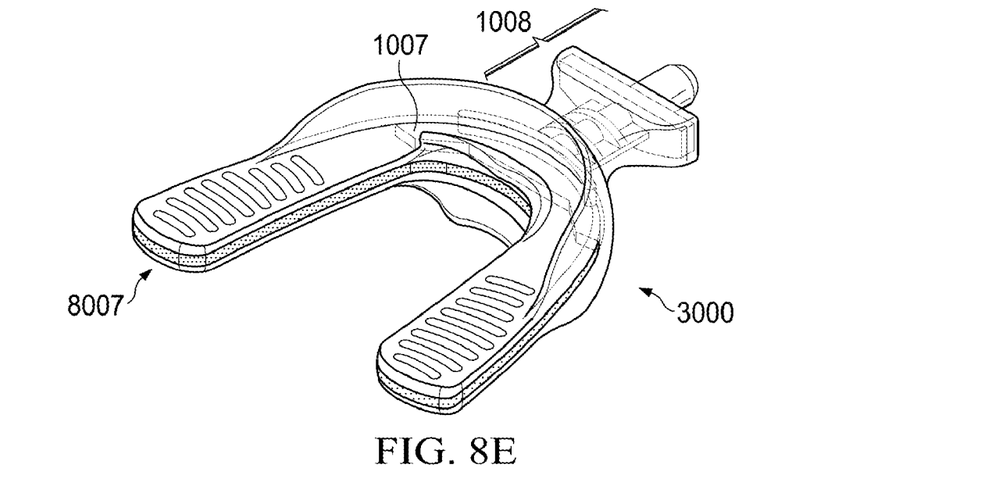
FIG. 8E shows the molded bite plate coating with the removable fluoride-releasing core snuggly fit between the upper and lower ends of the bite plate.

FIG. 8D shows the coating (3000) comprising a softer polymer capable of bending and opening to receive the removable fluoride-releasing core (8007). The coating (3000) also covers the stem (1008) on the truncated bite plate (1007). The tabs (3001) located on the coating (3000) fit snugly in the holes (8011) on the core with the fluoride-releasing material (8007), thus keeping the core (8007) in place during operation. Any shape can be used for the tabs and receiving holes, although for simplicity, cylindrical and circular shapes are shown here. FIG. 8E displays the removable fluoride-releasing (8007) and the core (1007) completely inserted into the coating 3000.

Figure 9A:
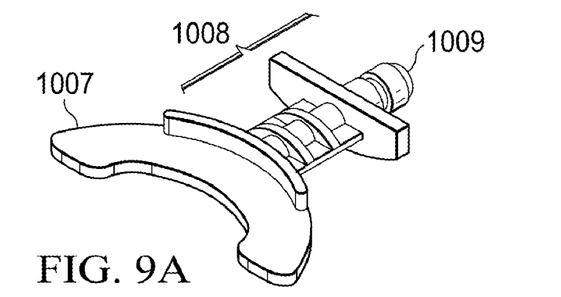
FIG. 9A shows a truncated version of the core from FIGS. 5A-B and 6.
Figure 9B:
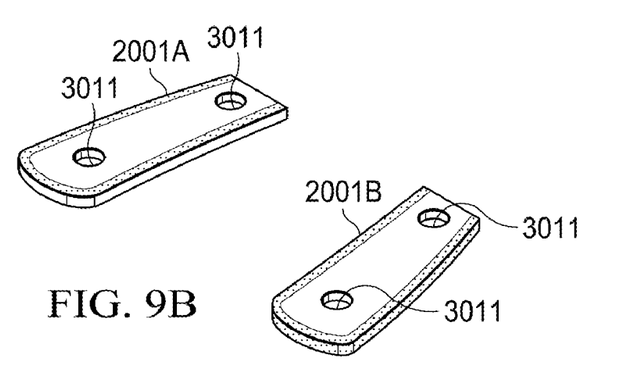
FIG. 9B displays a top view of a two-piece removable core comprising fluoride-releasing material.
Figure 9C:
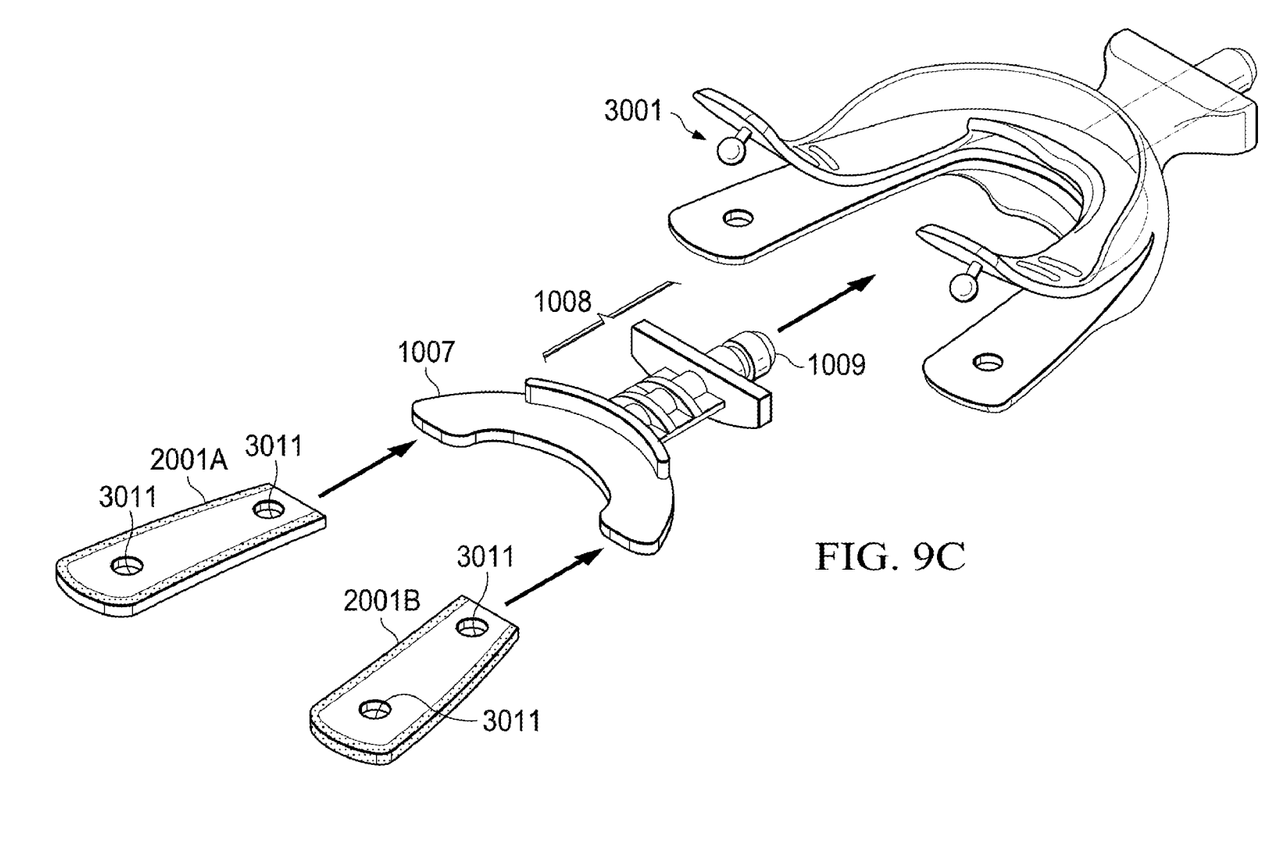
FIG. 9C displays the molded bite plate coating opened to receive the truncated bite plate with the stem and the removable core comprising fluoride-releasing material.

In yet another embodiment, the removable fluoride-releasing core can be modified as shown in FIG. 9B. Here, the removable fluoride-releasing core (2001A and 2001B) is two pieces that fit smoothly with the bite plate (1007) in FIG. 9A to form a U-shaped core. Here, the core (1007) is truncated in such a way as to maintain the U-shaped design and fits within the molded bite plate coating (3001) as before. The removable fluoride-releasing core can then be inserted into the molded bite plate (3000) and secured with tabs (3001). When aligned in the molded bite plate coating, the bite plate and two-piece core form a U-shape, as seen in FIG. 9C.

Figures 10, 11:
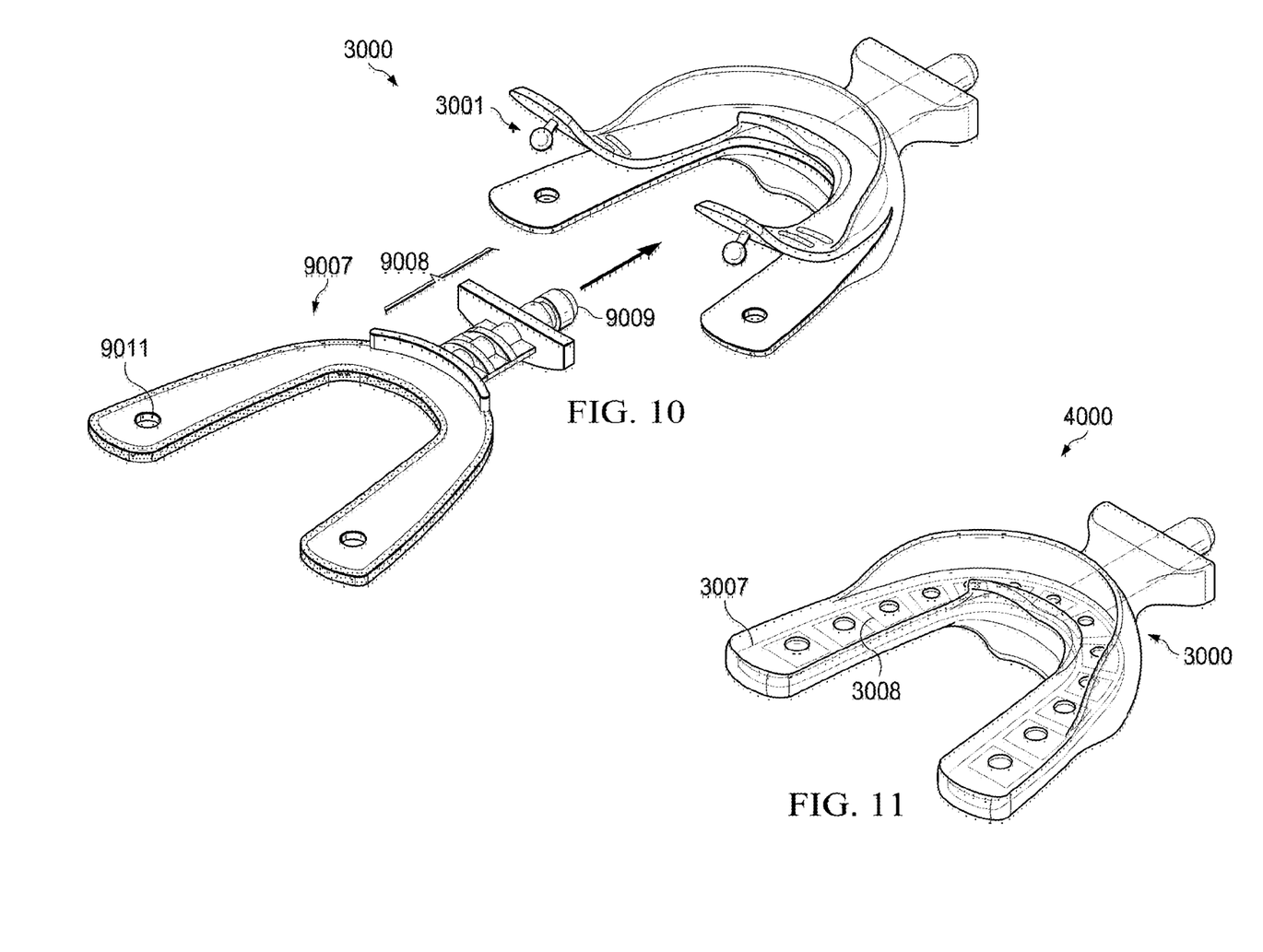
FIG. 10 displays a removable core with fluoride-releasing material. Here, the fluoride-releasing material is located on the core that also has a stem, which fits into a mating socket on the extraoral housing (not shown).
FIG. 11 displays a molded bite plate coating with a non-removable fluoride-releasing material on the core.

Alternatively, if a hard enough fluoride-releasing material or a hard enough support material is use, it can be used as the bite plate without any covering. FIG. 10 depicts such a situation.

FIG. 10 shows the removable fluoride-releasing core (9007) of the bite plate, typically made from a resin, metal or ceramic having a harder durometer than the outer surface and micronized fluoride containing filler, and providing sufficient rigidity to the stem (9008) so as to allow it to lockingly fit into the socket. Cylindrical shaft (9009) has a groove (not shown), into which jump ring fits. The stem also has the same locking pins (1011) and orientation pins (1114) as shown in FIG. 5B. Generally, plastics of at least 40 Shore D are used for the core, but metals or ceramics could also be used. An optional coating is provided over this core, and if used must be porous enough to allow fluoride transfer or have holes or a large cutout for same, and provides the final shape of the bite plate, as shown in FIG. 10. Such coating should be a biocompatible soft polymer of 40-70 Shore A, and particularly preferred is a medical grade, clear silicone. The core (9007) also has a hole (9011) for accepting a tab located on said coating to reversible bind said fluoride-releasing core.

In certain embodiments, the core can include colorants (non-toxic dyes or pigments) or sustained-release matrices with colorants (not shown) to lend color to the core. These colorants can be released on contact with saliva, such that the color of the core diminishes with use. Alternatively, a sustained-released matrix can be coated on the fluoride-releasing core.

FIG. 11 displays another bite plate (4000), wherein the fluoride-releasing material (3008) is coated onto the core (3007), which is molded into the bite plate coating (3000). In this particular embodiment, the core is not removable. The stem (2008) and shaft (2009) are not shown.

The following references are incorporated herein in their entireties for all purposes.

Arbabzadeh-Zavareh F, Recharge pattern of contemporary glass ionomer restoratives, Dent Res J (Isfahan). 2012 March; 9(2):139-45.

Austina, R. S., et al., The effect of increasing sodium fluoride concentrations on erosion and attrition of enamel and dentine in vitro, J Dent. 2010 October; 38(10):782-7.

Baturina O, Development of a sustained fluoride delivery system, Angle Orthod. 2010 November; 80(6):1129-35.

Beltrán-Aguilar, E. D., et al., Prevalence and Severity of Dental Fluorosis in the United States, 1999-2004, NCHS Data Brief Number 53, November 2010, available online at cdc.gov/nchs/data/databriefs/db53.htm.

de Francisco L. M., et al., Development and characterization of gelatin and ethylcellulose microparticles designed as platforms to delivery fluoride, Drug Dev Ind Pharm. 2012

Lin D. M., A polymeric device for delivery of anti-microbial and anti-fungal drugs in the oral environment: effect of temperature and medium on the rate of drug release, Dent Mater. 2003 November; 19(7):589-96.

Lynch E, et al., Multi-component bioactive glasses of varying fluoride content for treating dentin hypersensitivity, Dent Mater. 2012 February; 28(2):168-78.

Rosenblatt A, et al., Silver diamine fluoride: a caries "silver-fluoride bullet", J Dent Res. 2009 February; 88(2): 116-25.

Wu N., et al., Effect to demineralization and remineralization of enamel surface by fluorine, 2012 October; 30(5): 493-7.

U.S. Pat. No. 6,009,589
U.S. Pat. No. 4,044,762
U.S. Pat. No. 5,198,220
U.S. Pat. No. 5,718,924
US20120285574
US2008227046 et seq
US20120322018
61/624,242, filed Apr. 13, 2012
61/673,236, filed Jul. 18, 2012

What is claimed is:

1. A fluoride-releasing bite plate comprising:
   a) an intraoral bite plate comprising a sustained-release fluoride-releasing material intimately admixed with a 0.5-2% fluoride compound and intimately admixed with a color indicator amount augmented to match the expected fluoride depletion over time to indicate when fluoride is no longer released at a therapeutically effective concentration of at least 0.02% and it is time to replace the fluoride-releasing material, wherein said fluoride-releasing material is not a separate fluoride containing fluid applied to the bite plate;
   b) said intraoral bite plate having a substantially U-shaped surface for contacting an occlusal surface of teeth;
   c) said U-shaped bite plate having an outside edge having upper and lower rims to contact an upper and lower facial surfaces of teeth and gums;
   d) said U-shaped bite plate having an inside edge having optional upper and lower rims to contact at least a portion of an upper and lower lingual surfaces of teeth and gums;
   e) said U-shaped bite plate also having a connector, said connector comprising a cylindrical shaft having a snap-fit connector.

2. The fluoride-releasing bite plate of claim 1, wherein said fluoride compound is stannous fluoride or sodium fluoride or silver fluoride.

3. The fluoride-releasing bite plate of claim 1, wherein said fluoride-releasing material is micronized fluoride-containing filler in a polymeric substrate.

4. The fluoride-releasing bite plate of claim 1, wherein said bite plate comprising a polymer selected from the group consisting of methacrylate polymers, methacrylate copolymers, and mixtures thereof; a monomer selected from the group consisting of monomeric heterocyclic methacrylic esters, $C_3$-$C_4$ methacrylic esters, and mixtures thereof; and 0.5-2% non-toxic, biologically acceptable metal fluoride, wherein the ratio of the polymer to the monomer is from 1.25:1 to 1.75:1 by weight.

5. The fluoride-releasing bite plate of claim 1, wherein said bite plate comprises a polymeric silicone and stannous fluoride.

6. The fluoride-releasing bite plate of claim 1, wherein said bite plate comprises a polymeric silicone and sodium fluoride.

7. The fluoride-releasing bite plate of claim 1, wherein said bite plate comprises a silver fluoride.

8. The fluoride-releasing bite plate of claim 1, wherein said bite plate comprises a polymeric silicone and silver fluoride.

9. The fluoride-releasing bite plate of claim 1, further comprising a polymeric core having a coating or partial coating of fluoride-releasing polymer.

10. The fluoride-releasing bite plate of claim 1, further comprising a polymeric core having a coating or a partial coating of fluoride-releasing glass ionospheres.

* * * * *